United States Patent
Wang et al.

(10) Patent No.: US 10,126,289 B2
(45) Date of Patent: Nov. 13, 2018

(54) MULTIMODALITY CMOS SENSOR ARRAY FOR PHYSIOLOGICAL CHARACTERIZATION OF CELLS

(71) Applicant: Georgia Tech Research Corporation, Atlanta, GA (US)

(72) Inventors: Hua Wang, Atlanta, GA (US); Taiyun Chi, Atlanta, GA (US); Jongseok Park, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 410 days.

(21) Appl. No.: 15/050,002

(22) Filed: Feb. 22, 2016

(65) Prior Publication Data

US 2016/0245788 A1 Aug. 25, 2016

Related U.S. Application Data

(60) Provisional application No. 62/118,524, filed on Feb. 20, 2015.

(51) Int. Cl.
*G01N 21/64* (2006.01)
*G01N 33/483* (2006.01)

(52) U.S. Cl.
CPC ................. *G01N 33/4836* (2013.01)

(58) Field of Classification Search
CPC .............. G01N 33/6893; G01N 33/543; G01N 33/6863; G01N 2800/324; G01N 2800/325; G01N 2800/50; G01N 33/4836
See application file for complete search history.

(56) References Cited

U.S. PATENT DOCUMENTS

| 8,867,038 B2 * | 10/2014 | McCaffrey | B01L 3/502707 356/432 |
| 2015/0065372 A1 * | 3/2015 | Amir | G01N 33/6893 506/9 |

OTHER PUBLICATIONS

Wang et al., "Cell culture and cell based sensor on CMOS", 2014, IEEE Biomedical and Circuits and Systems Conference, 4 pages. (Year: 2014).*
H. Wang, et al., "A magnetic cell-based sensor," Lab Chip, 2012 pp. 4465-4471, vol. 12.
M. Schienle, et al., "A fully electronic DNA sensor with 128 positions and in-pixel A/D conversion," IEEE J. Solid-State Circuits, Dec. 2004, pp. 2438-2445, vol. 39, No. 12.
(Continued)

*Primary Examiner* — Kiho Kim
(74) *Attorney, Agent, or Firm* — Talem IP Law, LLP

(57) ABSTRACT

A multi-modality sensor for physiological characterization of cells can include an array of sensing pixel groups, each sensing pixel group comprising an array of sensing pixels; a plurality of signal conditioning blocks, each signal conditioning block coupled to a corresponding one sensing pixel group of the array of sensing pixel groups to process outputs of that sensing pixel group; and a controller providing signals for independent configuration of sensing modalities for each pixel of each sensing pixel group. The pixels of the multi-modality sensor support at least two sensing modalities by including an op amp that can be shared by at least two sensing circuits and including a photodiode. A cellular culture can be applied to the multi-modality sensor and a biological measurement can be performed on the cellular culture using at least two sensing modalities of the multi-modality sensor.

16 Claims, 13 Drawing Sheets

(56) References Cited

OTHER PUBLICATIONS

A. Manickam, et al., "A CMOS electrochemical impedance spectroscopy (EIS) biosensor array," IEEE Trans. Biomed. Circuits Syst., Dec. 2010, pp. 379-390, vol. 4, No. 6.

M. Jenkner, et al., "Cell-based CMOS sensor and actuator arrays," IEEE J. Solid-State Circuits, Dec. 2004, pp. 2431-2437, vol. 39, No. 12.

G. Medoro, et al., "A lab-on-a-chip for cell detection and manipulation," IEEE Sens. J., 2003, pp. 317-325, vol. 3, No. 3.

B. Jang, P. et al., "A CMOS fluorescent-based biosensor microarray," IEEE ISSCC Dig. Tech. Papers, 2009, pp. 436-437.

G. Patounakis, et al., "Active CMOS array sensor for time-resolved fluorescence detection," IEEE J. Solid-State Circuits, Nov. 2006, pp. 2521-2530, vol. 41, No. 11.

J. Park, et al., "A multimodality CMOS sensor array for cell-based assay and drug screening," IEEE ISSCC Dig. Tech. Papers, 2015, pp. 208-209.

B. Eversmann, et al., "A 128 × 128 CMOS biosensor array for extracellular recording of neural activity," IEEE J. Solid-State Circuits, Dec. 2003, pp. 2306-2317, vol. 38, No. 12.

H. Nakazawaa, et al., "Multimodal bio-image sensor for real-time proton and fluorescence imaging," Sens. Actuators B: Chem., Nov. 2011, pp. 14-20, vol. 180.

Y.-J. Huang, et al., "A self-powered CMOS reconfigurable multi-sensor SoC for biomedical applications," IEEE J. Solid-State Circuits, Apr. 2014, pp. 851-866, vol. 49, No. 4.

W. P. Chan, et al., "A monolithically integrated pressure/oxygen/temperature sensing SoC for multimodality intracranial neuromonitoring," IEEE J. Solid-State Circuits, Nov. 2014, pp. 2449-2461, vol. 49, No. 11.

* cited by examiner $Z_n = V/I_B, Z_5 = \Sigma Z_n/4, (n = 1, 2, 3, 4)$

MULTIMODALITY CMOS SENSOR ARRAY FOR PHYSIOLOGICAL CHARACTERIZATION OF CELLS

BACKGROUND

Researchers continuously pursue a better understanding of the physiological behaviors of living cells and tissues in order to further advance the frontiers of bioscience and biotechnology. The physiological behaviors and responses of wide-type and genetically modified cells and tissues are currently tested using cell-based assays. For example, during large-scale drug screening in the pharmaceutical industry, in vitro cultured cells for the cell-based assays are used to characterize certain properties, such as potency and toxicity, of chemical compounds for potential new drugs. The cell-based assays are also used, for example, in determining patient-specific treatments in personalized medicine, fast pathogen screening for epidemic disease detections, and detecting biohazards and pollutants in environmental monitoring.

However, cells are highly complex systems with numerous molecules operating in hundreds of pathways to maintain their proper functions, phenotypes, and physiological behaviors. With such a high level of complexity, the cells often undergo concurrent multiple physical responses when subjected to external biochemical stimuli or physiological condition shifts. Accurate characterization of these changes is difficult using conventional sensing technology.

SUMMARY

A sensor array is described herein that enables multiple physiological cellular characteristics to be measured. Multiple sensing modalities are provided as part of a single sensing pixel of the sensor array.

A single sensing pixel can include at least two sensing modalities. An efficient footprint is possible by sharing a single operational amplifier among the sensing circuitry. A grouping of sensing pixels can share a same readout circuitry while having independent control of sensing modality selection. An array of such sensing pixel groups can form a sensor array.

The sensor array can be operated to perform at least two sensing modalities on tissue or cells applied on the sensor. The at least two sensing modalities may be selected from electrical voltage recording, electrical impedance mapping, optical detection, thermal monitoring, and pH testing as examples.

BRIEF DESCRIPTION OF THE DRAWINGS

FIG. 12A shows the measured and simulated voltage gain and FIG. 12B shows the input-referred voltage noise power spectral density (PSD) of the sensing pixel.

DETAILED DESCRIPTION

A sensor array is described herein that enables multiple physiological cellular characteristics to be measured. Multiple sensing modalities are provided as part of a single sensing pixel of the sensor array. Various implementations of this multi-modality sensing enables living tissues and cells, such as a cardiomyocyte or neuron (for example, human or mouse neuron), to be characterized in multiple ways at effectively the same time (and in real-time) to achieve a comprehensive overall characterization of cellular physiological behavior changes in response to stimuli.

The multi-modality sensor array can be implemented with standard, low-cost complementary metal oxide semiconductor (CMOS) technology, which provides ease of fabrication, low power consumption, and ubiquitous utility. In the embodiments described herein, 130 nm or larger CMOS technology nodes are used (e.g., 130 nm, 180 nm, 250 nm, 350 nm, and the like).

Figure 1:
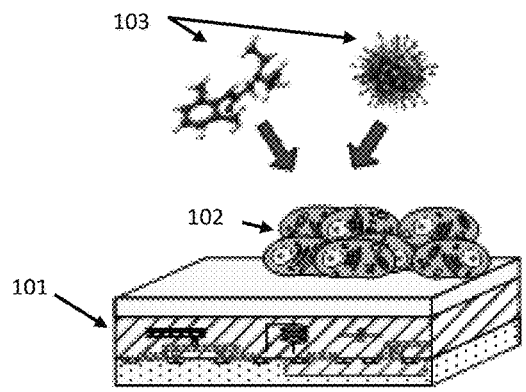
FIG. 1 shows a representation of a multi-modality sensor array chip illustrating a sensing environment.

FIG. 1 shows a representation of a multi-modality sensor array chip illustrating a sensing environment. Referring to FIG. 1, a multi-modality sensor array chip 101 can perform multi-modality sensing of cultured cells 102 (or tissue) placed on the chip 101 to capture the physiological behaviors of the cells 102 (or tissue). For example, sensing can occur before, during, and/or after various external biological or biochemical stimuli 103, such as chemical/drug or pathogen, are introduced to the cells to capture the physiological behaviors of the cells.

The sensing modalities available for the multi-modality sensor array chip 101 include, but are not limited to, electrical voltage recording, electrical impedance mapping, optical detection with shadow/opacity imaging or bioluminescence sensing, pH/acidity sensing, and thermal/temperature monitoring. The chip 101 provides multi-modality sensing since at least two modalities can be performed. The at least two modalities may be able to be performed at the same time and can be used to measure multiple physiological signals from a single cellular sample.

Each mode is used to characterize different physiological characteristics, for example, as shown in Table 1.

TABLE 1

| | Sensing Modality | Physiological Measurements | Sensing Circuits |
| --- | --- | --- | --- |
| Modality 1 | Electrical voltage recording | Cellular action potentials and local field potentials | Voltage amplifier (sub-Hz to kHz) |
| Modality 2 | Electrical impedance mapping | Cell attachment and intercellular communications | Applying Voltage (V) and Detecting the resulting Current (I) (kHz to MHz) |
| Modality 3 | Optical detection | Cell morphology changes (shape, etc.) and viability testing | Photodiode and amplifier |
| Modality 4 | Thermal monitoring | Environmental temperature variations | Temperature sensor |
| Modality 5 | pH/Acidity testing | Cell viability and cell attachment | ISFET based pH sensor and amplifier |

As indicated in the Table 1, the electrical voltage recording mode can be used to measure cellular action potentials and local field potentials; electrical impedance mapping mode can be used to detect cellular attachments and cell-to-cell connections; optical detection can be used to measure cellular morphology changes such as shape and cellular viability testing; thermal monitoring can be used to measure environmental temperature variations; and pH/acidity testing can be used to detect changes in pH for cell viability, cell attachment, and cell response. It should be understood that reference to voltage excitation is intended to enable cell/tissue impedance measurement and is not intended to refer to electro-chemical, biochemical reactions and the like.

Figure 2:
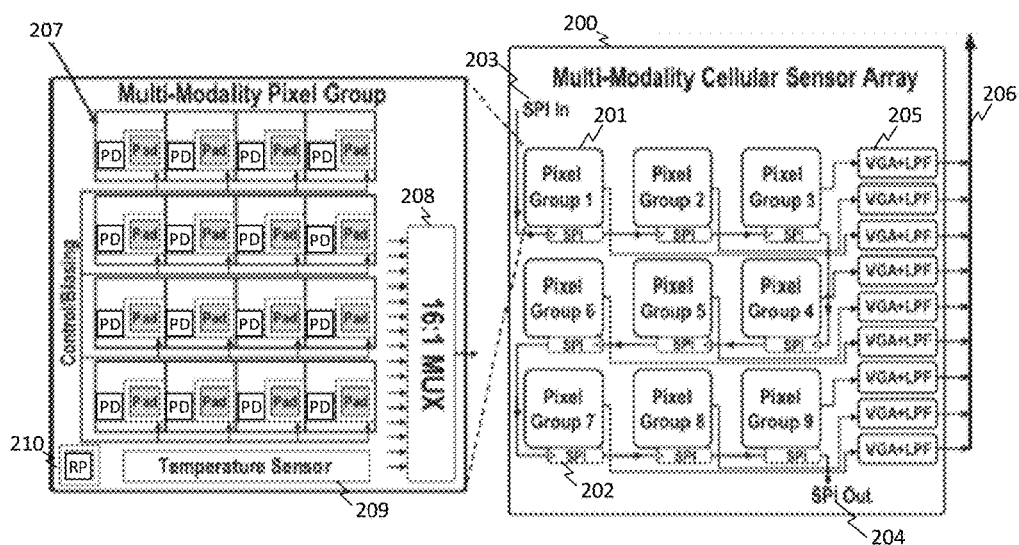
FIG. 2 shows an example illustration of a multi-modality sensor array on a chip.

FIG. 2 shows an example illustration of a multi-modality sensor array on a chip. Referring to FIG. 2, a multi-modality cellular sensor array 200 can include an array of sensing pixel groups 201. Each sensing pixel group 201 receives control signals from a controller for independent configuration of sensing modalities for each sensing pixel of each sensing pixel group 201.

An array of independently controlled multi-modality sensing pixels can enable several sensing modes for a same sample at effectively the same time (and even in real-time). For example, electrical voltage recording and electrical impedance mapping sensing may perform characterization of a same sample of cardiomyocytes or other cells during the administration of a drug. In another example, impedance mapping and optical shadow imaging may perform measurements of a same sample neuron aggregates or other cells, where the optical shadow imagining component can provide 2-dimensional location and area information to evaluate where aggregates are seeded, and impedance mapping can be used to extract sensor surface information regarding the cell's electrical impedance change and evaluate cell attachment.

Returning to FIG. 2, in some cases, the controller can include a serial-to-parallel interface (SPI) 202 for each sensing pixel group 201 (that when connected in a daisy chain formation can be programmed by shifting the signals from SPI-In 203 to SPI-Out 204). Each sensing pixel group 201 is further connected to a corresponding signal processing block 205, which then provides the chip outputs 206. A sensing pixel group 201 contains an array of sensing pixels 207. A multiplexer (MUX) 208 can be included to select which of the sensing pixels 207 is providing the signal output to the signal processing block 205, enabling a reduction in circuitry.

The number of sensing pixel groups 201 in the array and the number of sensing pixels 207 within a sensing pixel group 201 can vary depending on the design constraints of the sensor array. In the example illustrated in FIG. 2, the multi-modality cellular sensor array is implemented with an array of 9 sensing pixel groups containing 16 sensing pixels each. However, it should be understood that arrays of other sizes may also be used.

In some cases, a temperature sensor 209 can be included for thermal monitoring sensing. A single reference pad 210 can be included for each sensing pixel group as well. In one implementation, each sensing pixel 207 may be implemented as a tri-modality sensing pixel circuit. Additional features of a sensing pixel group 201 can include those described with respect to FIGS. 4 and 5.

The circuitry for electrical voltage recording, electrical impedance mapping, and ISFET (ion-sensitive field-effect transistor) pH/acidity testing generally involves operational amplifiers. Incorporating multiple sensing modalities into a single sensing pixel can be difficult if the entire circuitry of each modality is incorporated wholly and independently. A multi-modality sensing pixel circuit design is provided in which a single operational amplifier can be shared by multiple sensing circuits.

Figure 3A:
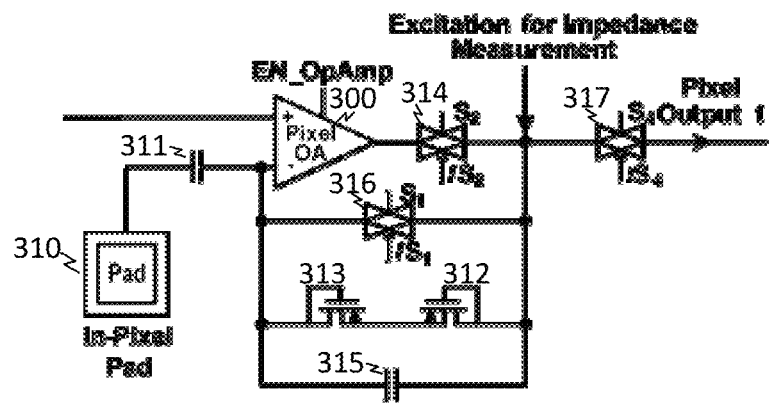
FIG. 3A illustrates an example configuration of a multi-modality sensing pixel circuit supporting voltage recording and impedance mapping.
Figure 3B:
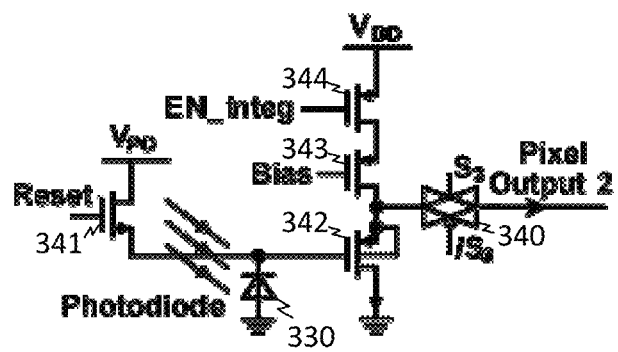
FIG. 3B illustrates example photodiode circuitry that can be included in a multi-modality sensing pixel.

FIG. 3A illustrates an example configuration of a multi-modality sensing pixel circuit supporting voltage recording and impedance mapping and FIG. 3B illustrates example photodiode circuitry that can be included in a multi-modality sensing pixel. In the example configuration of FIG. 3A, two circuits share a common operational amplifier (op amp) 300 and one in-pixel pad 310 that is connected to an inverting input of the op amp 300 through a DC blocking capacitor 311.

In this example, the two circuits supported by the sensing pixel circuitry are a voltage recording circuit and an impedance sensing circuit. The voltage recording circuit can use a differential measurement scheme involving the op amp 300 and the impedance sensing can use two configurations: a voltage excitation mode that bypasses the op amp 300 and a current sensing mode that uses the op amp 300 to amplify a signal. This is accomplished because in addition to the op amp 300, the sensing pixel circuitry includes two transistors 312, 313, switch 314, capacitor 315, and switches 316 and 317. The two transistors 312 and 313 are connected as pseudo resistors in a feedback loop from a node at the output of the op amp 300 to the inverting input of the op amp 300.

The switch 314, controlled by a control signal S2, selectively connects the op amp 300 to that node to which the two transistors 312, 313 connect. The capacitor 315 is provided parallel to the feedback connected transistors 312, 313. Also parallel to the two transistors 312, 313 and the capacitor 315 is a bypassing switch 316 controlled by signal S1. The switch 317 controlled by signal S3 can be used to control whether a signal is to be output from the sensing pixel. For example, the switch 317 is closed during a voltage excitation process for impedance measurement, but the switch 317 is open to output the signal during the voltage recording and the impedance current sensing.

In more detail, the control signals S1, S2, and S4 can be used to select the sensing modality and settings for the sensing pixel. For example, the sensing pixel can be configured for voltage recording with the op amp 300 on (using the op amp enable signal EN_OpAmp signal), signal S1 low (for open) and signals S2 and S4 high (for closed). Similarly, for performing as a current sensor in the impedance sensing modality, the op amp 300 is on (using EN_OpAmp signal), signal S1 is low (for open), and signals S2 and S4 are high (for closed). The sensing pixel can be configured for impedance sensing in voltage excitation form by turning the op amp 300 off (using EN_OpAmp signal), signals S2 and S4 low (for open) and signal S1 high (for closed) so an excitation signal (as indicated at the node in FIG. 3A) can bypass the op amp 300 and be fed directly to the In-pixel pad 310 for excitation of a sample for impedance measurement (this node is the same node that connects to the feedback loops to the op amp 300). The total in-pixel circuitry occupies a reduced physical footprint as a result of sharing the op-amp 300.

In the example configuration shown in FIG. 3B, when a photodiode 330 and sensor circuit is included in a sensing pixel, a second output can be included the multi-modality sensing pixel. The output can be controlled by a control signal S3 applied to a switch 340. The particular optical sensor circuitry can be any suitable configuration. In the illustrated example, an active sensing pixel sensor architecture is employed that includes an NMOS reset transistor 341 (receiving a reset signal to bring the photodiode cathode voltage to $V_{PD}$), a PMOS source-follower transistor 342 (connected to photodiode output as a common source amplifier), and a bias transistor 343 (receiving a bias voltage) and a buffer transistor 344 (receiving EN_INTEG signal) providing a PMOS cascode load. During optical sensing, NMOS reset transistor 341 is OFF and the photodiode 330 generates a photon current. The current is integrated over the total parasitic capacitance of the photodiode cathode node, and the integrated voltage is buffered by the source follower transistor 342.

The switches 314, 316, 317, 340 described with respect to FIGS. 3A and 3B may be implemented as bilateral switches or other transmission gates.

Figure 4:
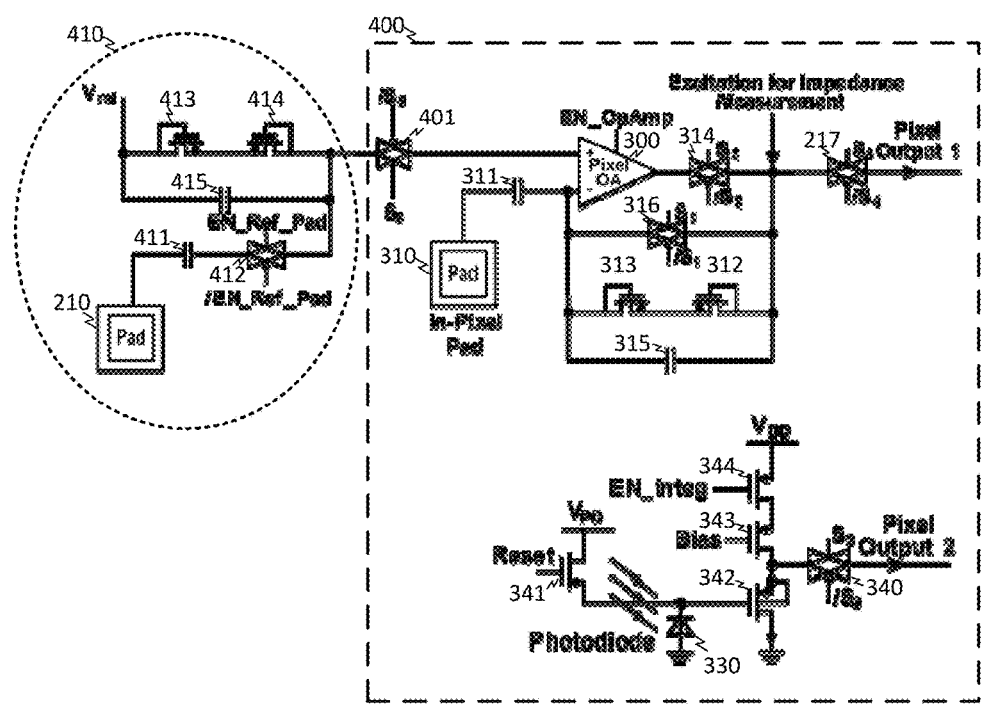
FIG. 4 illustrates an example implementation of a tri-modality sensing pixel circuit and shared sensing pixel group reference pad.

FIG. 4 illustrates an example implementation of a tri-modality sensing pixel circuit and shared sensing pixel group reference pad. Referring to FIG. 4, the example implementation of a tri-modality pixel 400 contains one voltage recording sensor, one impedance sensor (sensing/excitation), and one optical sensor, which can be implemented as described with respect to FIGS. 3A and 3B. The tri-modality sensing pixel 400 is selectably connected by switch 401, controlled by signal S5, to the sensing pixel group reference pad circuitry 410, which can implement the reference pad 210 and corresponding circuitry in a sensing pixel group 201 such as described with respect to FIG. 2. The switch 401 connects a signal from the reference pad circuitry 410 to the non-inverting input of shared op amp 300 and may be located within the sensing pixel 400.

The sensing pixel group reference pad 210 can be coupled to a DC blocking capacitor 411 and controllably connected to the other voltage reference circuitry through switch 412, which is controlled by a reference pad enable signal (EN_Ref_Pad). The sensing pixel group reference pad circuitry includes two transistors 413, 414 connected as pseudo resistors in series from a reference voltage, Vref, and a capacitor 415 connected in parallel to the two transistors 413, 414. This circuitry can be included to help control the DC output voltage of the op amp 300.

The reference pad enable signal is used during voltage recording to implement a differential measurement scheme to suppress the common-mode noise and offset in the measurements. When the switch EN_Ref_Pad is on, the reference pad 210 samples the background potential and noise of the nearby cellular environment, and this background potential is subtracted by the op-amp 300 to achieve the differential measurement.

As with switches 314, 316, 317, and 340, the switches 401 and 412 may be implemented as bilateral switches or other transmission gates.

Each tri-modality sensor pixel 400 may have two electrical outputs. One output is from the shared op amp circuitry; and the other output is from the optical sensor. Whether a signal is provided on the two electrical outputs is controlled by control signals S3 and S4. Of course, in some cases, a single output is provided from each sensing pixel for selection by MUX 208.

Advantageously, the described circuitry enables multiple sensing modalities to occur at effectively the same time. The sensing pixel circuitry also enables independent configuration of each sensing pixel within each sensing pixel group to perform different sensing modalities. For example, one sensing pixel may be performing voltage recording while another is performing optical sensing. In some cases, voltage recording and optical sensing may be carried out at the same time in a same sensing pixel, but the outputs selected at different times.

Figure 5:
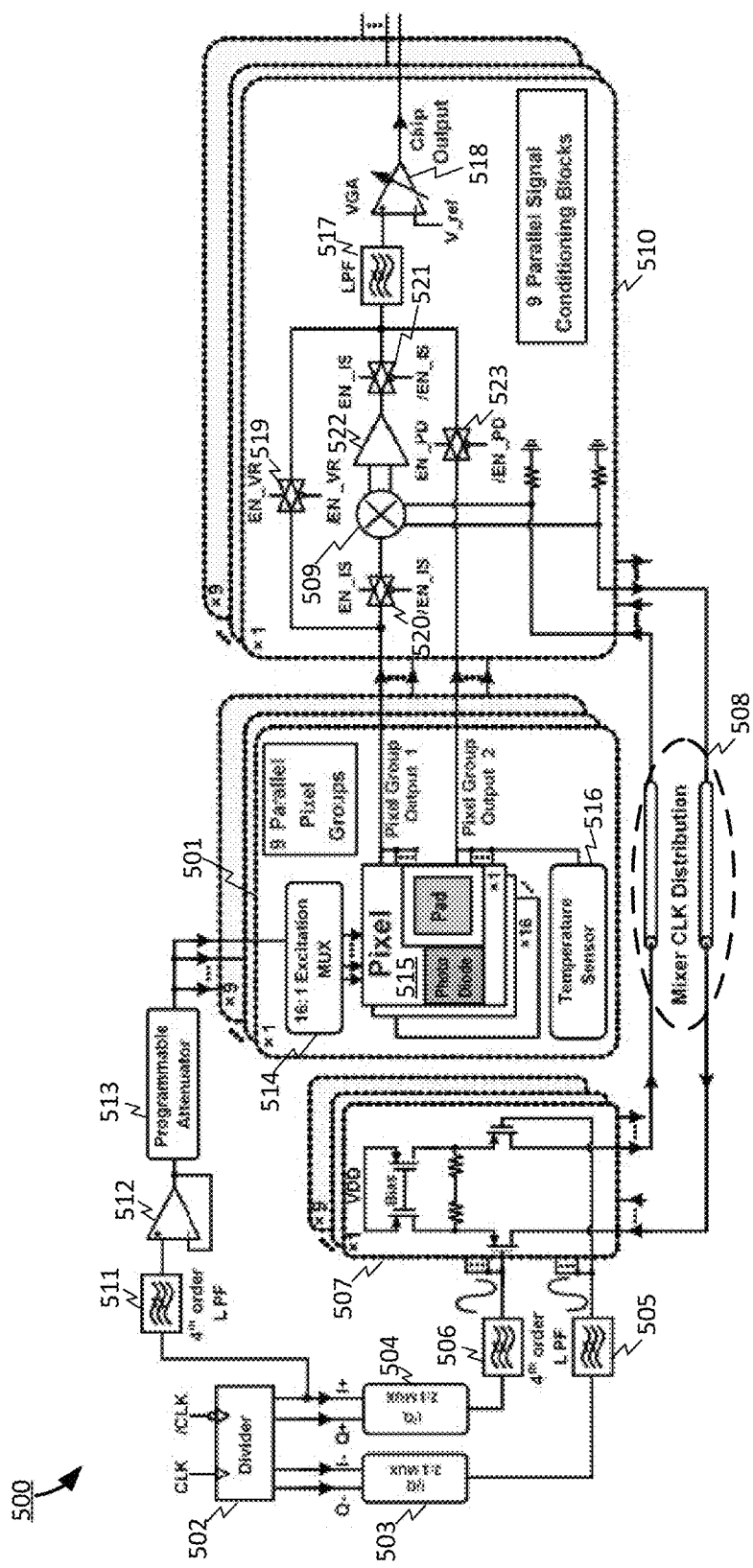
FIG. 5 shows a schematic representation of an example multi-modality cellular sensor array.

FIG. 5 shows a schematic representation of an example multi-modality cellular sensor array. Referring to FIG. 5, an external clock signal input (CLK, /CLK) drives the timing of the sensing circuitry on the chip 500 (and in the sensing pixel groups 501) to a desired frequency. A quadrature signal generator can be used to generate quadrature signals to support impedance mapping functionality. The quadrature signal generator may be a divide-by-two circuit 502. The divide-by-two circuit 502 generates in-phase (I) and quadrature (Q) signals (I−, Q−, I+, Q+) from the incoming clock.

A first 2:1 MUX 503 can be included to perform the selection of either the I− or Q− signal and a second 2:1 MUX 504 can be included to perform the selection of either the I+ or Q+ signal. The selected I and/or Q signals may pass through low pass filters 505, 506 before going to a buffer 507 for each of the sensing pixel groups 501 (which may be one implementation of sensing pixel group 201). The buffer 507 is coupled, via a transmission line 508 (Mixer CLK Distribution), to drive a down-conversion mixer 509 in the corresponding signal conditioning block 510 (which may be one implementation of conditioning block 205) for coherent detection of a sensing mode. In particular, within a parallel signal conditioning block 510, the mixer 509 is used to perform quadrature down-conversion to detect the complex impedance of a tissue sample at a sensing pixel level. That is, for the current sensing component of impedance detection, a buffer circuit (507) for each sensing pixel group 501 is provided that couples a selected in-phase or quadrature signal to the signal conditioning blocks 510 via mixer CLK distribution transmission lines 508 and to the down-conversion mixer 509. The selected in-phase or quadrature signal can be selected using the first 2:1 MUX 503 to select between I− and Q− and the second 2:1 MUX 504 to select between I+ and Q+.

The current sensing and down-converting of the sensed current using quadrature mixing into baseband enables measurement of both the real and imaginary parts of the impedance. Both the real and imaginary components of impedance are detected because cellular impedance is not only the real part (resistive), but a large portion, namely the cellular membrane, is also imaginary (capacitive). During current sensing, the current from the nearby cellular environment flows through the sensing pixel electrode of a sensing pixel enabled for current sensing and is then converted to a voltage signal by the feedback capacitor 315 shown in FIGS. 3A and 4. The frequency dependence of the capacitive loads in the sensing pixel 515 may be later calibrated.

For the voltage excitation component of the impedance detection, the I+ signal generated by the divide-by-two circuit 502 is taken out and used to generate a voltage excitation signal. This impedance testing signal generator can include a low pass filter 511, an op-amp 512, and a programmable attenuator 513. The programmable attenuator 513 can be used to control the amplitude of the voltage excitation signal. A MUX 514 at each sensing pixel group 501 can be used to select the sensing pixel(s) 515 for performing voltage excitation (e.g., applying voltage signals to achieve impedance mapping). Thus, the voltage excitation signal can be buffered onto a selected sensing pixel(s) (e.g., to the node indicated in FIGS. 3A and 4) of a sensing pixel group 501 via the MUX 514. Each sensing pixel 515 of a sensing pixel group 501 may be implemented such as described with respect to sensing pixel 400 of FIG. 4 and a common reference pad for the sensing pixel group 501 can be used as described with respect to FIG. 4.

In operation, for both the voltage recording and impedance detection, the sensing electrode (in-pixel pad 310) of each sensing pixel is AC-coupled to the cell medium to remove the DC voltage offset and drift of the electrode-electrolyte interface. Thus, the DC blocking capacitor 311 can block the DC voltage offset and drift at the electrode-electrolyte interface. This DC blocking capacitor also inhibits DC currents charging the cells so that cellular damage can be avoided.

Figure 6:
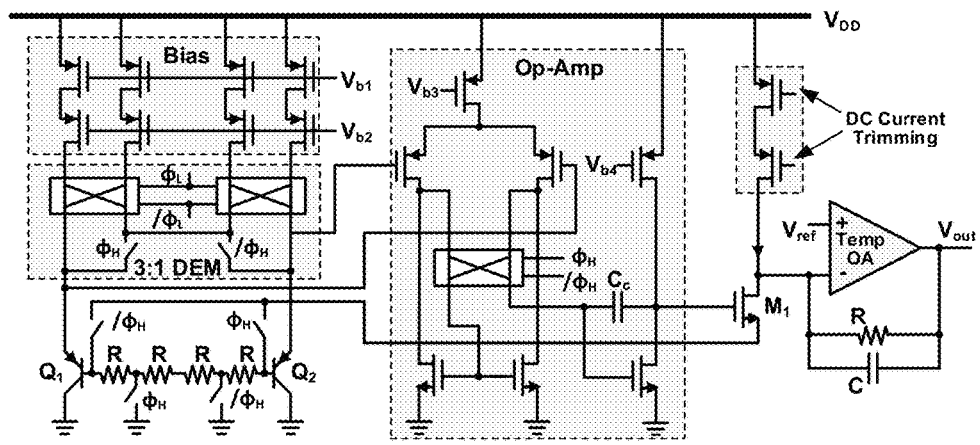
FIG. 6 shows an example of a temperature sensor circuit.

In addition, a temperature sensor 516 can further be included in each sensing pixel group. A selected sensing pixel output and the temperature sensor reading can be output to the corresponding signal conditioning block 510. FIG. 6 shows an example of a temperature sensor circuit. The core of the temperature sensor is a Proportional-to-Absolute-Temperature (PTAT) circuit. Two substrate PNP transistors (Q1 and Q2) are biased by four identical cascode PMOS current sources with the current ratio of 3:1. Dynamic element matching (DEM) and chopper-stabilization schemes can be used to minimize component mismatches in the PMOS current sources, the resistors, and the PNP transistors, and cancel the op-amp input DC offset. Several sets of complementary switches controlled by $\Phi_L$ and $\Phi_H$ perform the DEM and chopping operations. The DC current offset of the transistor $M_1$ is suppressed by the cascode PMOS trimming current. Each sensing pixel group can include this independently controlled temperature sensor circuit. The temperature sensors for the sensing pixel groups can share the same current trimming signal.

Returning to FIG. 5, the LPF 517 in the signal conditioning block corresponding to the sensing pixel group to which the temperature sensor circuit belongs can be used to suppress element mismatches and DC offset as well as complete the DEM and chopping operations from the temperature sensor circuit.

The temperature information can be used, for example, as a "sanity check" to verify that temperature has not changed or that the data is not biased due to unexpected temperature shifts.

Turning again to the signal conditioning block, each signal conditioning block 510 includes a low pass filter 517 (LPF) and variable gain amplifier 518 (VGA). The LPF 517 is used to filter out the supply line noise and the VGA 518 is used to amplify the signal to overcome the noise in the circuit.

Switches are used to configure the corresponding signal conditioning block 510 for the appropriate sensing modality. The signal conditioning blocks can be configured for each sensing mode by voltage recording switch 519 controlled by signal EN_VR, two current sensing switches 520, 521 controlled by EN_IS (with one located before the mixer 509 and the other located after an amplifier 522 at the mixer's output), and photodiode switch 523 controlled by EN_PD.

For example, enabling the voltage recording switch 519 allows the signal from the output 2 of a sensing pixel 515 to pass through to the LPF 517 and amplifier 518 and enabling the photodiode switch 523 allows the signal from the output 2 of a sensing pixel 515 to pass through to the LPF 517 and amplifier 518; however, enabling the two current sensing switches 520, 521 passes the signal from output 1 of the sensing pixel 515 through the mixer 509 and amplifier 522 before outputting through the LPF 517 and amplifier 518. Switches 519, 520, and 521 can be implemented as bilateral switches or other transmission gate. Not shown is the controller providing the signals for the switches of the signal conditioning block or the switches of the sensing pixel groups, such as the SPI 302 of FIG. 3.

Additional circuitry for the optical sensor component (other than the filtering and amplification provided by the signal conditioning block) is optional because each sensing pixel can include a complete optical sensing circuit and photodiode. The two outputs of a sensing pixel 515 can be selectively connected to the corresponding signal conditioning block 510 by a MUX (not shown). This MUX can be implemented as described with respect to MUX 208 of FIG. 2.

The array of sensing pixels 515 in a sensing pixel group 501 can share the processing circuitry through timesharing under selection by the MUX (e.g., MUX 208). The MUX for a sensing pixel group selects an enabled sensing pixel and its sensing signal to output to the corresponding conditioning block. The switching through the sensing pixels can occur on the order of milliseconds, which is sufficient for biological applications since biological processes tend to occur on the order of seconds, minutes, hours, and days. Time sharing/time interleaving can be performed to read out the sensing pixels in a manner that provides multiple sensing modalities to be performed on a sample at effectively the same time (for purposes of testing the biological process).

Figure 7:
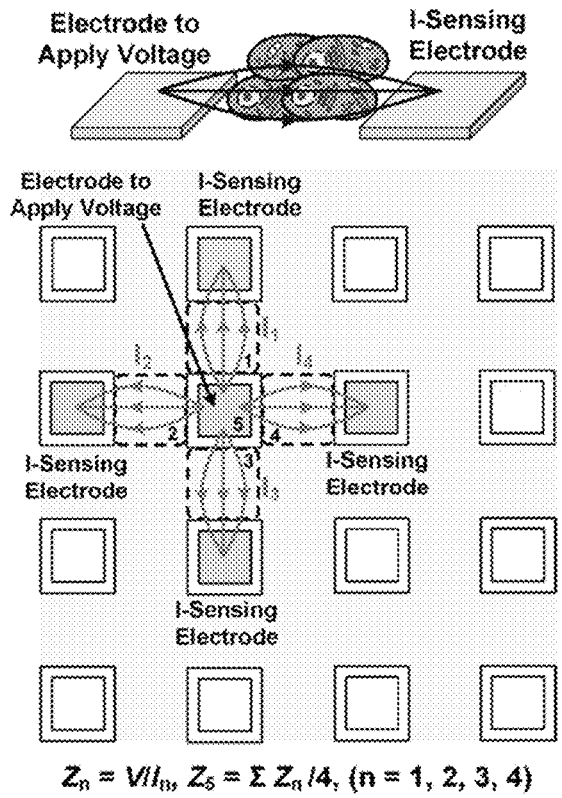
FIG. 7 shows an example implementation of an electrical impedance measurement that can be carried out by a few nearby sensing pixels.

FIG. 7 shows an example implementation an electrical impedance measurement that can be carried out by a single sensing pixel group. Referring to FIG. 7, since each sensing pixel of a sensing pixel group can be configured independently of others, an electrical impedance measurement can be accomplished by selecting one of the sensing pixels to be configured for voltage excitation and its neighboring four sensing pixels to be configured for current sensing. This example implementation can be useful in characterizing the cell location, tissue structure, and cell attachment to the surface. One pixel is selected to apply a voltage signal through its electrode, and a resulting cell/tissue current distribution is generated through the finite cell/tissue impedance. Adjacent four pixels are then sequentially enabled for the current sensing (I-sense electrodes). By measuring the AC currents through the four nearby pixels In (n=1, 2, 3, 4), the cellular impedance $Z_n$ (n=1, 2, 3, 4) between the voltage electrode and its adjacent I-sense electrode are measured. The cellular impedance on top of the voltage electrode $Z_5$ can also be calculated as the average of the impedance values measured with the four nearby I-sensing electrodes.

Figure 8C:
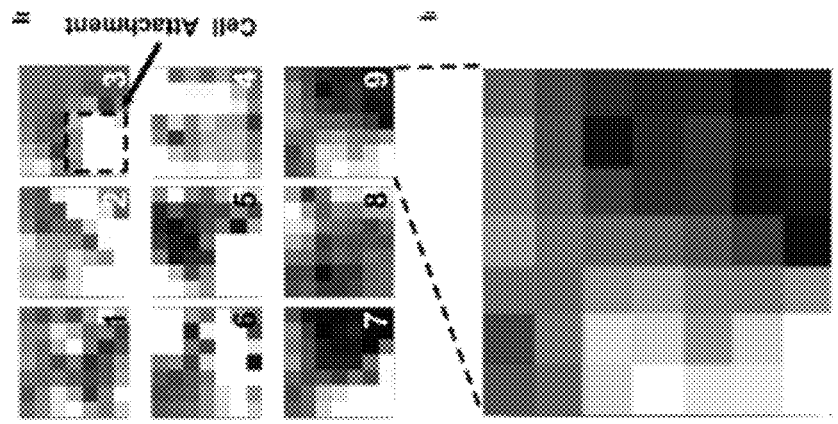
FIGS. 8A-8C illustrate characterization of cells on an example multi-modality chip having electrical impedance mapping and optical sensing.
Figure 8B:
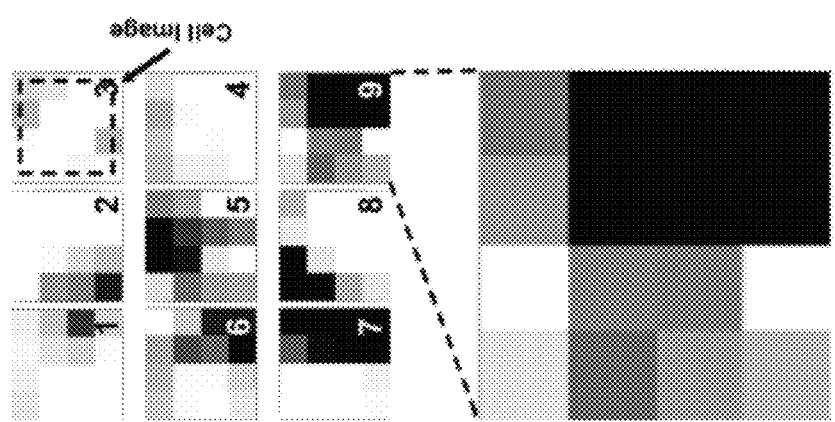
Figure 8A:
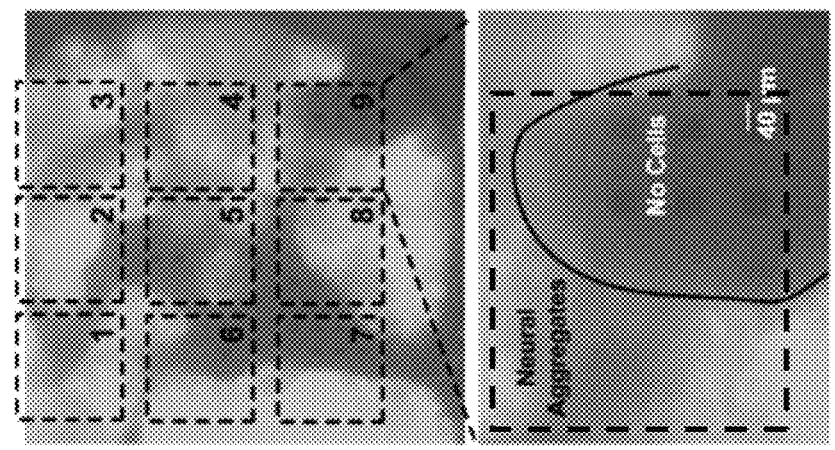

FIGS. 8A-8C illustrate characterization of cells on an example multi-modality chip having electrical impedance mapping and optical sensing. By incorporating both electrical impedance mapping and optical sensing on a same chip in a manner that can perform the sensing on a same portion of a sample (not necessarily at the same time), improved characterization can be accomplished. For example, ensuring proper cell attachment is the first step in performing a cell assay. The combination of electrical impedance mapping and optical sensing can be used to identify proper cell attachment (and even identify loss of attachment over time).

FIG. 8A illustrates a fluorescent image of one implementation of the multi-modality sensor array with 9 sensing pixel groups, each sensing pixel group having 16 sensing pixels, on which neural aggregates are applied. The expanded view shows a close up of a high magnification fluorescent image of sensing Pixel Group 9. The fluorescent image was taken by a microscope and is used as reference to show the location of the cells on the chip. FIG. 8B shows an output of the chip when configured to perform optical shadow imaging of the same cell sample used in the reference. The lighter color indicates lower intensity and the darker color indicates higher intensity. The optical shadow imaging shows a very strong correspondence to the reference images. As can be seen in the expanded view optical shadow image of sensing Pixel Group 9 with resolution of 4×4 sensing pixel group, the dark area covering the right, lower 6 sensing pixels corresponds to the region identified in the expanded fluorescent image having no cells. FIG. 8C shows an output of the chip when configured to perform electrical impedance mapping of the same reference cell sample. In this implementation, a resolution of 7×7 is possible for a sensing pixel group (because information between electrodes can be identified).

The electrical impedance mapping provides a measurement of the surface attachment of the cells to the chip. Examining optical shadow imagining measurements may not be enough to completely characterize the attachment of a 3-dimensional cell to the chip surface. For example, fluorescent shadow imagining and optical shadow imaging provide a top-down view of the cell, but do not measure the actual attachment of the cell to the surface of the chip. However, the impedance mapping mode is capable of determining how the cell is attached. In the example shown in FIG. 8C, sensing Pixel Group 3 of the impedance mapping mode includes a region highlighted as a dotted region. The dotted region shows a strong cell attachment in the bottom left corner of sensing Pixel Group 3 that is not evident in the same sensing Pixel Group 3 in the optical shadowing image of FIG. 8B since the cell image in FIG. 8B appears that cells are located throughout (indicated by the low(er) intensity values across most of the sensing pixel group). This advanced characterization of a cell can be possible using a multi-modality sensing array.

Figure 9:
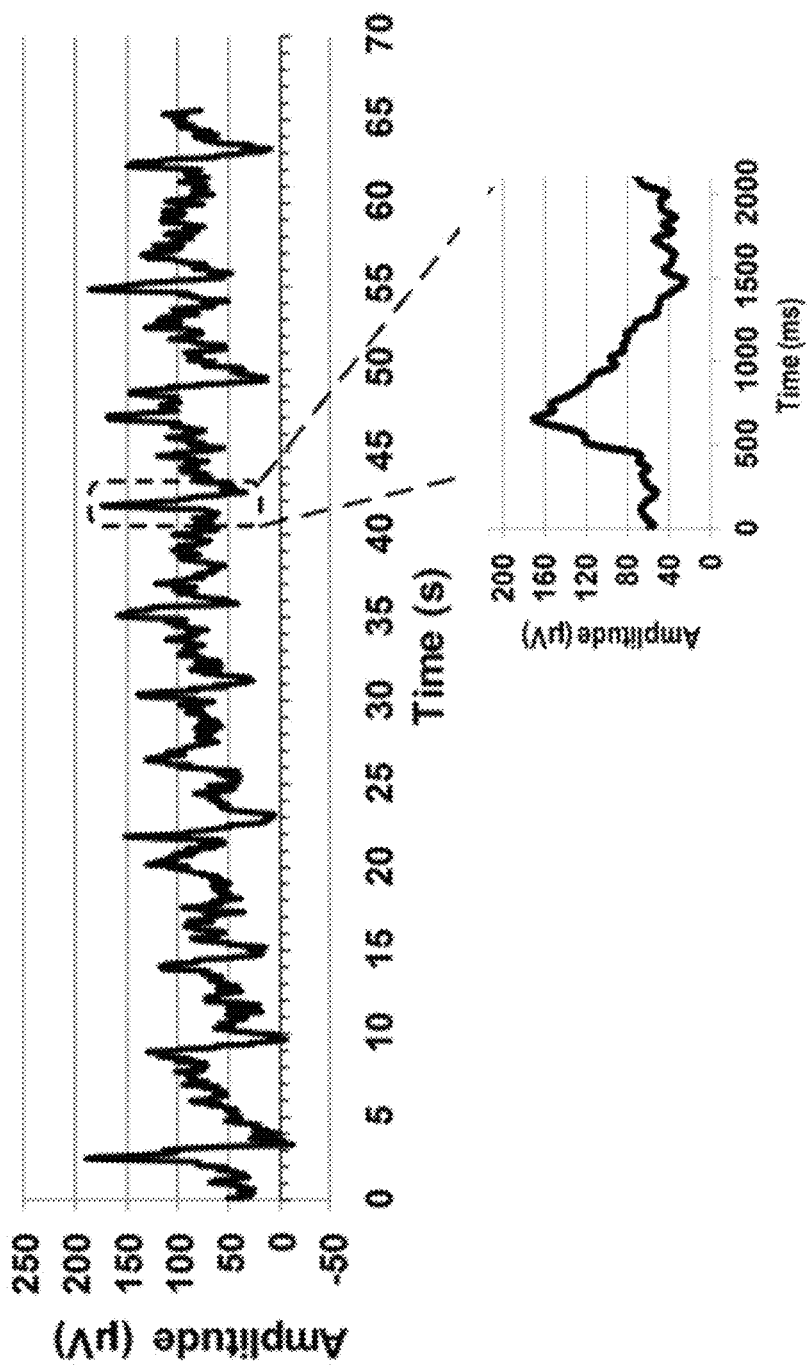
FIG. 9 illustrates characterization of cells on an example multi-modality chip having voltage recording and electrical impedance mapping.

FIG. 9 illustrates characterization of cells on an example multi-modality chip having voltage recording and electrical impedance mapping. The inclusion of voltage recording and impedance mapping can facilitate drug screening. For example, extracellular potential recording of cardiomyocytes (CMs) can be performed to identify cardiac beating rate and impedance measurements can be taken (e.g., with time sharing) throughout administration of a drug that affects beating rate to check that the changes in beating rate are not due to other effects (that can be identified from a change in the impedance measurements).

EXPERIMENTAL EXAMPLES

Figure 10:
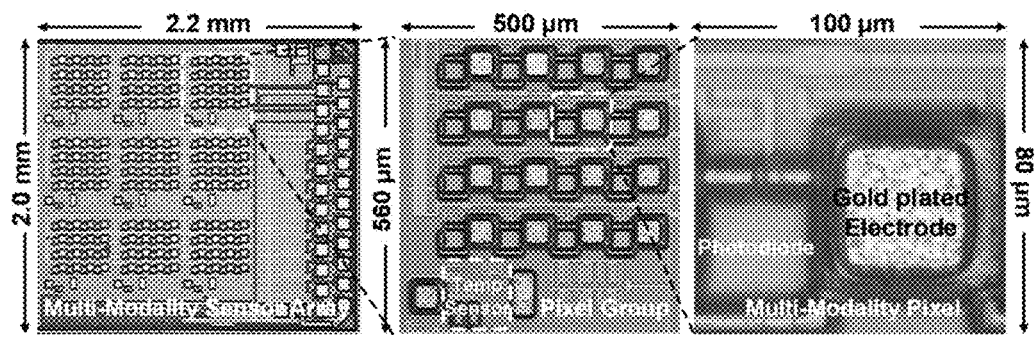
FIG. 10 shows a chip micrograph of a multi-modality CMOS sensor array chip according to an example implementation.

A multi-modality CMOS sensor array chip was manufactured. The chip occupies 2.2 mm×2.0 mm in a standard 0.13 µm CMOS process. FIG. 10 shows a chip micrograph of a multi-modality CMOS sensor array chip according to an example implementation. The close-in views of the sensing pixel group (560 µm×500 µm) and the tri-modality sensing pixel (100 µm×80 µm) are also shown. The CMOS sensor array chip includes the circuitry shown in FIGS. 3-6 with nine parallel signal conditioning circuit blocks processing the outputs from the corresponding parallel sensing pixel groups having 16 sensing pixels each.

In the voltage recording/impedance mapping circuit of each tri-modality sensing pixel, the capacitors 311 and 411 are 11.2 pF and capacitor 315 is 0.68 pF. These capacitors 311, 411, and 315 were implemented as metal-insulator-metal (MIM) capacitors, and were placed beneath the sensing electrode for reduction in the circuit size. The transistor length/widths of 4 µm/680 nm for transistors 312, 313, 413, 414 to provide MOS-bipolar pseudo resistors of 230 GΩ. Since the impedance measurement mode operates from 500 kHz to 4 MHz, the described circuitry is sufficient to characterize the cellular impedance.

In the example implementation, the sensing pixel op amp 300 is a one-stage common-source amplifier with a current-mirror active load. The op amp 300 can perform as a low-noise sensing pixel voltage amplifier that amplifies two types of extracellular electrical signals: local-field potentials (LFPs) and action potentials (Aps). For example, the LFPs from neurons represent the averaged electrical activity of the neurons surrounding the recording site with a typical bandwidth from sub-Hz to 300 Hz. The action potentials (Aps) from, for example, cardiomyocytes or neurons, represent cellular electrical activity under excitation and typically with a higher frequency range from 300 Hz to 10 kHz.

The in-band closed-loop gain of op amp 300 is set by the capacitance ratio of the capacitor 311 to the capacitor 315 as 23.5 dB. The MOS-bipolar pseudo-resistors 312, 313 are used in the feedback path to bias the inverting input of the op amp 300. This 230 GΩ resistor (from transistors 312, 313) and the feedback capacitor 311 (0.68 pF) provide a low cut-off frequency of 0.5 Hz. This low cut-off frequency enables the LFPs to be monitored.

In practice, the MOS-bipolar pseudo-resistor can suffer from a leakage current. Due to its large resistance value (230 GΩ), even a small leakage current can create a substantial DC voltage drop across the resistor and thus a DC offset between the inverting input and the output of the op-amp. Extensive simulations across process corners and temperature settings (from 15° C. to 45° C.) were performed to characterize this DC voltage drop. The simulated DC voltage drop is less than 230 mV, ensuring negligible effects on the op-amp operation.

The non-inverting input of the in-pixel op amp 300 is biased by a reference voltage $V_{ref}$ of 1.4V, shared among the 16 tri-modality sensing pixels 207, 400 in each sensing pixel group 201. With a similar leakage current and DC voltage drop of the two pseudo resistors 413 and 414, the DC output voltage of the in-pixel op amp 300 can closely track the reference voltage $V_{ref}$.

In the optical sensing circuit in each tri-modality sensing pixel, one reverse-biased p+/nwell/psub photodiode with size 40 μm×40 μm is used as the photodiode 330. The PMOS source follower transistor 342 was fabricated with its body node tied to its source terminal to cancel the body effect for improved linearity. In addition, a correlated double sampling (CDS) scheme was used to suppress the reset noise, DC offset, and the device flicker noise. Each photodiode was surrounded by a metal shield to minimize the crosstalk from the adjacent sensing pixels.

In the signal conditioning circuit blocks, the LPFs 511 were implemented using programmable second-order Sallen-Key LPFs (with 3-bit controls on cutoff frequency) and the VGAs 512 were implemented with a 5 bit VGA with a programmable gain from 0 dB to 18 dB as the output buffer for the chip. The LPFs and VGAs directly process the output signals from the voltage recording, optical detection, and temperature sensing modes, while the impedance measurement outputs are first down-converted by the mixers and then processed by the LPFs and VGAs. An on-chip Serial-to-Parallel-Interface (SPI) was integrated for digital programming.

Figure 11:
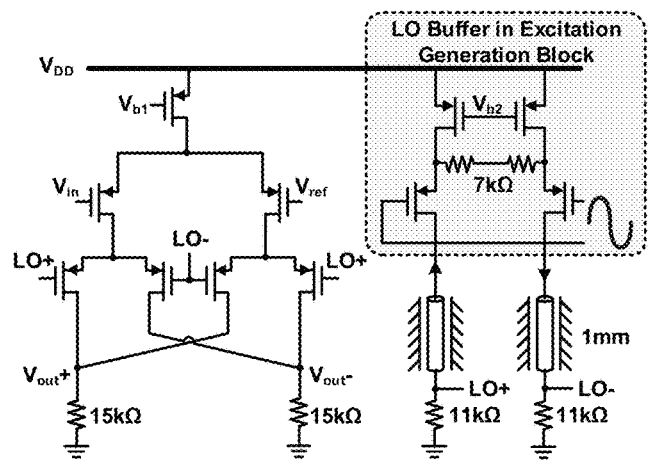
FIG. 11 shows a schematic of a down-conversion mixer used in the manufactured chip.

FIG. 11 shows a schematic of a down-conversion mixer used in the manufactured chip. Referring to FIG. 11, a PMOS-based pseudo-differential double-balanced mixer is used to down-convert the measured impedance detection signal. The mixer LO signals are derived from the LO buffer in the excitation generation block, and the I/Q LO signals are sequentially applied to the mixer for quadrature down-conversion and coherent detection of complex cellular impedance. Due to the long on-chip routing between the mixer and the excitation generation circuit (around 1 mm), shielded transmission line structures were used to distribute the LO signal on-chip with minimized coupling to other circuits.

The divide-by-2 circuit 502 was implemented using current-mode-logic latches to generate the quadrature LO signals. Glitches during the divided-by-2 operation are removed using a Schmitt trigger. The harmonic tones in the voltage excitation signal will generate harmonic currents through the cells. Since these harmonic currents can be down-converted by the mixer through its harmonic mixing and thus distort the impedance measurement, a 4th order programmable Sallen-Key LPF 511 is employed to suppress these harmonic tones in the voltage excitation signal and achieve a 30 dB 3rd-order harmonic rejection. The programmable attenuator 513 is also employed to scale the voltage excitation signal and avoid saturating the current sensing circuit.

Electrical Measurement Results

To suppress the 60 Hz power-line noise in the measurement, the setup was powered by D-type batteries and enclosed in a grounded metal box for electromagnetic isolation. The digital programming signals for the CMOS chip were generated by the digital I/O channels in a Data-AcQuisition module DAQ (Measurement Computing USB 1608G), while the nine parallel analog outputs from the chip were read by the parallel analog channels of the DAQ module and digitized by its 16-bit analog-to-digital-convertors (ADCs).

The performance of the voltage recording mode was characterized using a Dynamic Signal Analyzer (Agilent 35670A) by measuring the voltage gain, bandwidth, and the input-referred noise power spectral density (PSD) of the sensing sensing pixels.

Figure 12A:
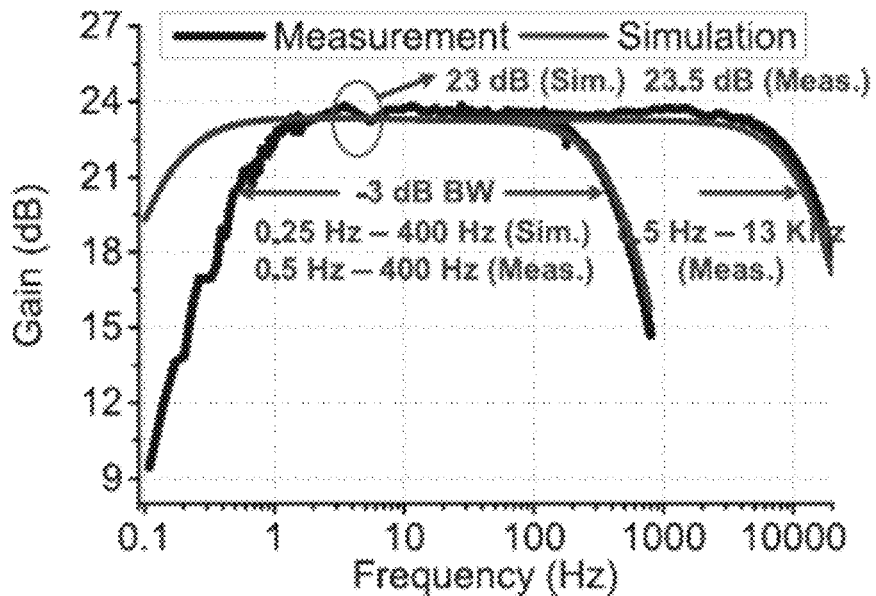
FIGS. 12A and 12B show plots of voltage recording mode characteristics.
Figure 12B:
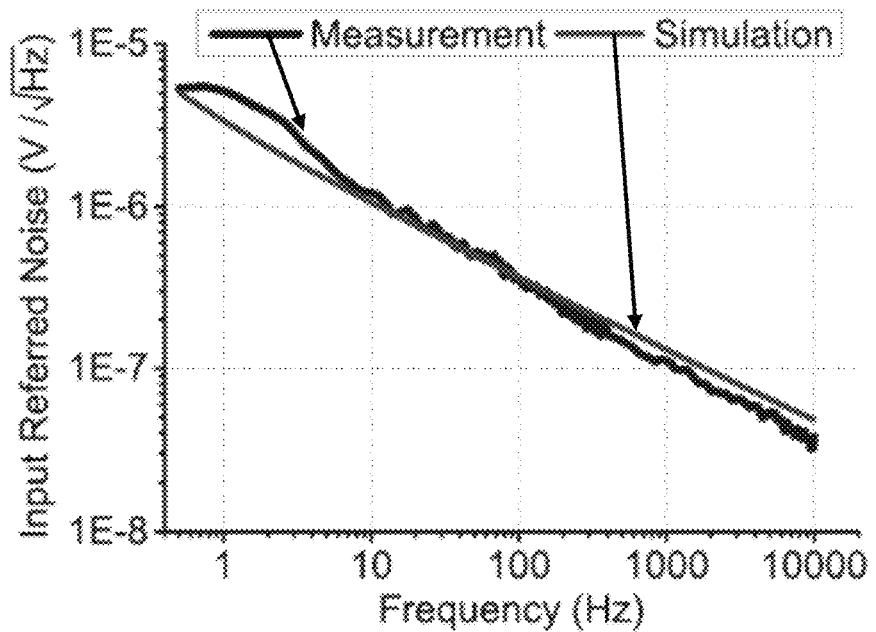

FIGS. 12A and 12B show plots of voltage recording mode characteristics. FIG. 12A shows the measured and simulated voltage gain and FIG. 12B shows the input-referred voltage noise power spectral density (PSD) of the sensing pixel. Referring to FIG. 12A, the measured low cut-off frequency is 0.5 Hz with a mid-band gain of 23.5 dB, sufficient to detect the low-frequency cellular local field potentials. The difference between the simulated and measured low cut-off frequency is due to the inaccuracy in the modeling of the MOS-bipolar pseudo resistor. Referring to FIG. 12B, the averaged integrated noise from 0.5 Hz to 400 Hz is 11.1 $\mu V_{rms}$ with a 3σ variation of 3.7 $\mu V_{rms}$. The averaged integrated noise from 0.5 Hz to 10 KHz is 12.7 $\mu V_{rms}$ with a 3σ variation of 3.5 $\mu V_{rms}$. The measurement result matches well with the simulation. The DC power consumption of the sensing pixel op-amp is 165 μW with a supply voltage of 3.3V and a reference voltage of 1.4V.

Figure 13:
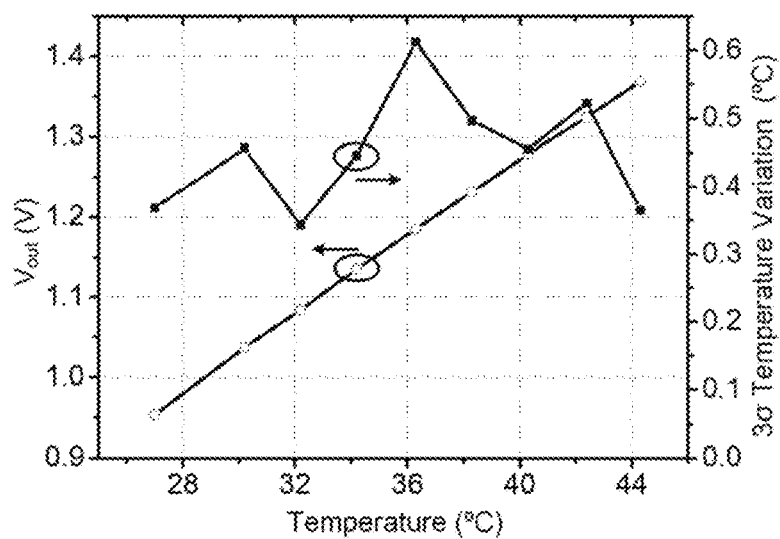
FIG. 13 shows the measured averaged output voltage and the 3σ variations from the nine independent on-chip temperature sensors versus the ambient temperature.

The temperature sensor was characterized using a temperature chamber (Half Cube Model 105). FIG. 13 shows the measured averaged output voltage and the 3σ variations from the nine independent on-chip temperature sensors versus the ambient temperature. The temperature sensor response slope is 24 mV/° C. The maximum 3σ temperature variation of the nine temperature sensors is within 0.6° C.

Figure 14:
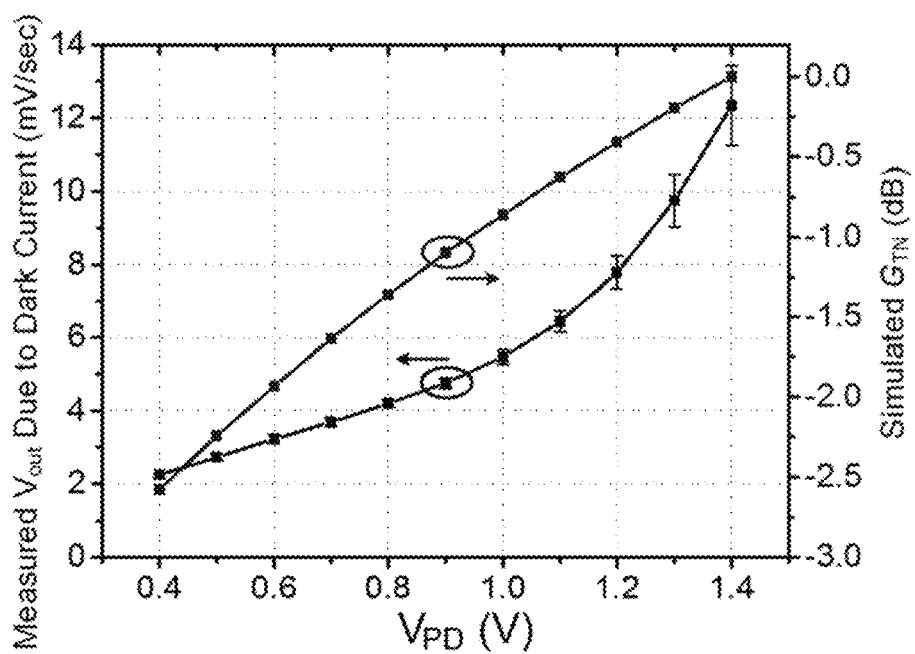
FIG. 14 shows the measured sensing pixel output voltage, $V_{out}$, due to the photodiode dark current and simulated normalized transducer gain, $G_{TN}$ of the in-pixel optical sensor versus photodiode biasing voltage $V_{PD}$.

For the optical detection, the pixel photodiode dark current was characterized at different photodiode biasing voltages $V_{PD}$. FIG. 14 shows the measured sensing pixel output voltage, $V_{out}$, due to the photodiode dark current and simulated normalized transducer gain, $G_{TN}$ of the in-pixel optical sensor versus photodiode biasing voltage $V_{PD}$. The measurement was performed in a dark room with a reset frequency of 0.05 Hz and a 5% duty cycle. The dark current variation across the entire chip is marked using the error bar at each $V_{PD}$ value in FIG. 14. As can be seen in FIG. 14, the measured dark current increases substantially if the photodiode biasing voltage is above 1V. However, the transducer gain $G_T$ of the optical detection also increases with its reverse biasing voltage due to the decreased diode junction capacitance, as shown in (1)

$$G_T = \frac{V_{out}}{P_{inc}} = \frac{R_\lambda T}{C_{par}} = \frac{QE\lambda qT}{C_{par}\hbar c}, \qquad (1)$$

where $V_{out}$ is the output voltage of the source follower shown in FIG. 3B (and FIG. 4), $P_{inc}$ is the incident light power, $R_\lambda$ is the diode responsivity, T is the integration time, $C_{par}$ is the total parasitic capacitance of the photodiode cathode node, QE is the quantum efficiency, λ is the wavelength, q is the electron charge, $\hbar$ is the Planck constant, and c is the speed of the light.

The simulated normalized transducer gain $G_{TN}$ is also plotted in FIG. 14, where the normalized transducer gain $G_{TN}$ is defined as $$G_{TN} = 20\log\left(\frac{G_T}{G_{T|V_{PD}=1.4V}}\right). \qquad (2)$$

Assuming a constant diode responsivity $R_\lambda$ versus biasing voltage, then the normalized transducer gain is the capacitance ratio versus photodiode reverse-biased voltage. Considering the trade-off among the dark current, the transducer gain, and the dynamic range, the photodiode biasing voltage is chosen at 1V for general cellular optical measurements, such as optical shadow imaging. However, for measurements with a low light intensity, e.g., bioluminescence experiments, a low $V_{PD}$ of 0.4V is used to minimize the dark current.

Biological Measurement Results

Gold plating was utilized to treat the sensing pixel electrode to enhance the electrode biocompatibility and robustness for biological measurements. Other than the gold plating, this CMOS multi-modality sensor array chip does not require any other post processing step. This makes the solution compatible with low-cost mass production and useful for high-volume applications such as drug screening and development.

The CMOS chip was mounted on a PCB using conductive epoxy. A Polydimethylsiloxane (PDMS) structure provides electrical isolation and seals the bonding wires while maintaining the packaging biocompatibility. The CMOS chip surface was directly exposed to the cell samples and the culture medium. A standard 35 mm plastic cell culture dish with drilled-out bottom was mounted on the PCB to hold the cellular samples.

The types of cells included in the examples below are human cardiomyocytes (CMs) derived from human embryonic stem cells (ESC), mouse neurons (MNs) derived from a progenitor MN green-fluorescent-protein (GFP) reporter mouse ESC line, and a human ovarian cancer cell line (HeyA8-F8). These on-CMOS cultured cells were utilized for multiple cell measurements and cell-based assays by using the CMOS multi-modality sensor chip. These experiments demonstrate the functionalities of the CMOS multi-modality sensor array.

Human cardiomyocytes (CMs), mouse neurons (MNs), and human ovarian cancer cells were successfully cultured on the CMOS multi-modality sensor chip. The cell culture methods were performed as follows.

Human Cardiomyocytes. Human ESCs are first cultured in a monolayer until confluence. Next, cardiomyocytes are directly differentiated through the use of small molecules Gsk3 inhibitor and Wnt inhibitor for 14 days. Finally, the CMOS chip is sterilized using 70% ethanol and coated with a Matrigel matrix as a protein mixture layer to enhance cell culture and attachment. Cardiomyocytes are then seeded onto the CMOS chips as either single cells or aggregated cardiospheres.

Mouse Neurons. The TG25 Mouse ESCs are first cultured in a monolayer in the presence of the leukemia inhibitory factor (lif) until reaching 70% confluence. Next, 1000 cell embryoid bodies (EBs) are formed by forced aggregation in micro-wells for 24 hours. EBs are further cultured in suspension on a rotary culture system for 5 more days in the presence of neural induction factors, smoothened agonist (SAG, 1 µM) and retinoic acid (RA, 2 µM). Finally, the CMOS sensor chip is sterilized using 70% ethanol and coated with laminin, an epithelial cell adhesion glycoprotein. EBs of 1 ml are then transferred to the chip surface for maturation and later assay measurements.

Ovarian Cancer Cells. For culturing the ovarian cancer cells (HeyA8-F8), the CMOS chip surface is sterilized by 70% ethanol and then washed three times with sterile Phosphate Buffered Saline (PBS). To increase cell adhesion to the chip surface, 0.1% gelatin is added onto the chip for 30 minutes before being aspirated. Gelatin is a derivative of collagen and one type of common extracellular matrix protein. Ovarian cancer cells are then seeded directly onto the CMOS chip and allowed to attach before adding 1 mL of cell culture media.

Extracellular Voltage Recording

Figure 15:
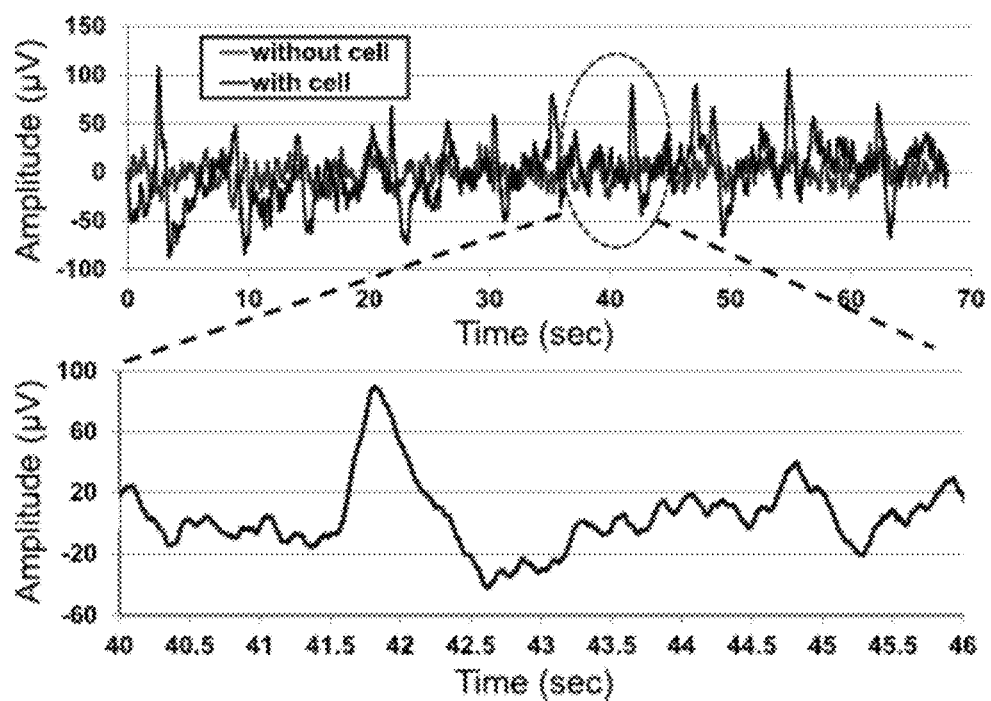
FIG. 15 shows the measured input-referred extracellular voltage recording signals with and without active CM cells for the experimental example.

Human CMs were used for demonstrating the extracellular voltage recording of the CMOS multi-modality sensor array chip. FIG. 15 shows the measured input-referred extracellular voltage recording signals with and without active CM cells for the experimental example. As can be seen in FIG. 15, spontaneous beatings are detected and easily distinguished from the sensor noise floor. The measured period of the autonomous cell beating spikes is about 5-7 s, which is further confirmed by visual inspections through a stereo microscope.

Real-Time 2D Cellular Impedance Mapping for Cell Detachment Experiment

Cell adhesion to the culture surface is essential for the growth and viability of mammalian cells as well as the formation of tissues. Moreover, cell attachment can be utilized to perform cell migration assays, which is widely used in cancer studies. The cells and the culture medium have different impedance, and typically the cells present higher cellular impedance values. Thus, the cell attachment to the CMOS chip surface can be detected by the 2D impedance mapping. Note that optical detections, for example, shadow imaging or fluorescence microscopy, only yield the 2D distribution of the cells, and cannot provide the surface attachment information (see e.g., FIGS. 8A-8C and corresponding description).

To perform a cell detachment experiment, an excitation frequency of 1 MHz and an excitation voltage of 10-100 mV was applied. On-CMOS cultured human ovarian cancer cells (HeyA8-F8) were used in this example. The cell detachment was triggered by applying Accutase® cell detachment solution to the culture medium, where Accutase is a natural enzyme mixture with proteolytic and collagenolytic enzyme activity. It has been widely used in cell detachment, analysis of cell surface markers, virus growth assays, and tumor cell migration assays. After the human ovarian cancer cells were seeded onto the CMOS multi-modality sensor array chip, Accutase was applied to the culture medium, and a real-time 2D impedance mapping was measured versus time. Typically, Accutase suspends the cells within 15 minutes. Therefore, after the Accutase administration, the measured 2D cellular impedance was expected to first decrease and then stay constant after the cells are fully detached from the CMOS chip surface.

Figure 16:
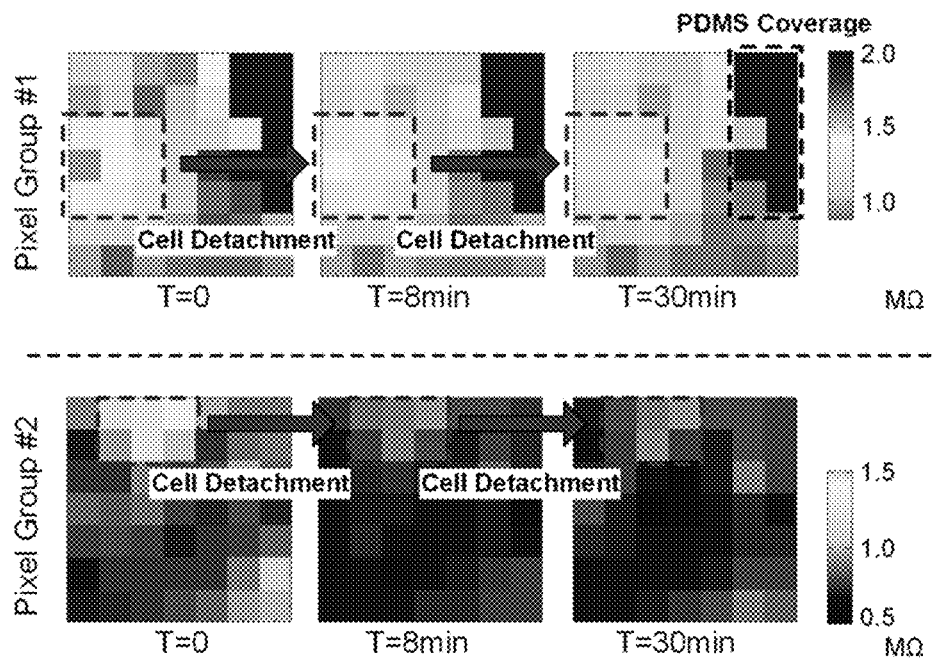
FIG. 16 shows the measured impedance mapping results of two sensing pixel groups after Accutase® administration in the experimental example.
Figure 17:
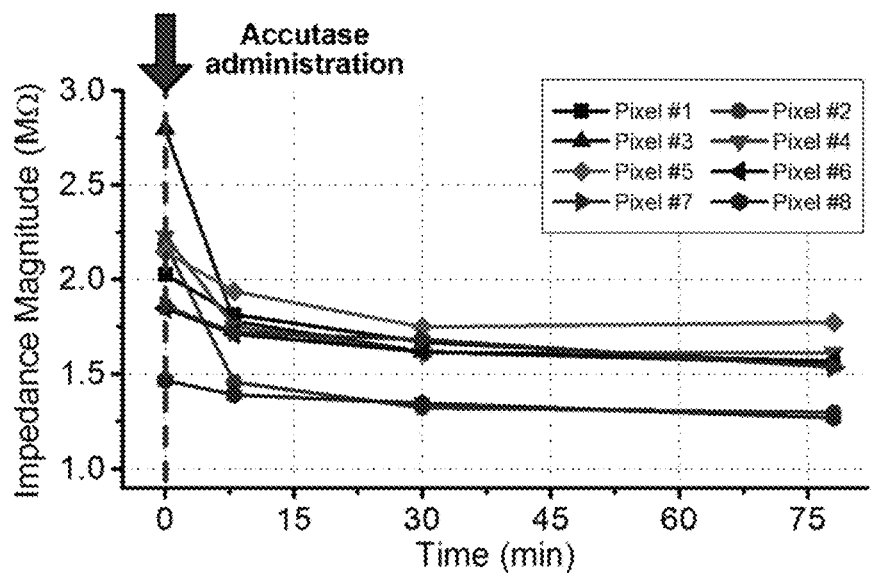
FIG. 17 shows the real-time measured impedance values at 8 different sensing pixels after Accutase® administration in the experimental example.

FIG. 16 shows the measured impedance mapping results of two sensing pixel groups after Accutase administration in the experimental example. A rapid impedance decrease can be seen after 8 mins, indicating the cell detachment. FIG. 17 shows the real-time measured impedance values at 8 different sensing pixels after Accutase administration in the experimental example. The measured impedance values first decrease when Accutase is applied and then become constant after full cell detachment. These results align well with the mechanistic effect of Accutase. Therefore, the multi-modality sensor array chip can be utilized in cell surface adhesion and cell migration assays, for example studying tumor cell migrations.

Real-Time Bioluminescence Measurement

The human ovarian cancer cells (HeyA8-F8) can constitutively express firefly luciferase. Thus, when luciferin is added to the culture medium, these cancer cells will exhibit luminescence emission. This is because luciferase catalyzes the reaction of luciferin, oxygen, and adenosine triphosphate (ATP) to yield unstable oxyluciferin, which then emits luminescence light during its relaxation back to the ground energy state. In general, upon the luciferin administration, the luminescence emission will reach its peak after about 5 minutes and can be detected for about half an hour, depending on the number of cells and the luciferin concentration. The bioluminescence information can be used to verify the viability of the HeyA8-F8 cancer cells and can be further extended to other bioluminescence cell-based assays.

Figure 18:
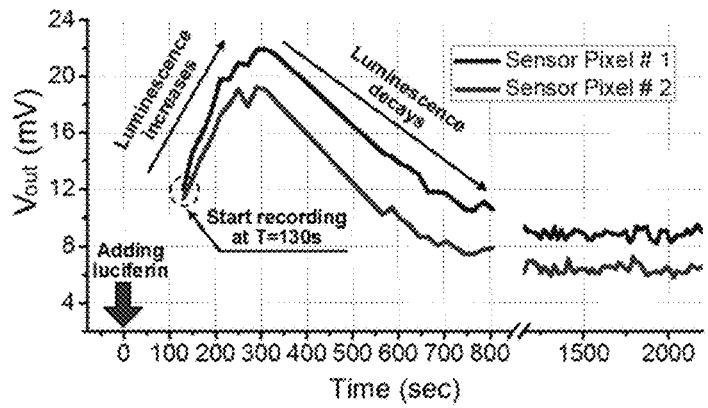
FIG. 18 shows real-time measured optical sensor outputs at two different sensor pixels for the bioluminescence experiment with human ovarian cancer cells.

Since the intensity of the bioluminescence light is generally weak, the background noise, such as the photodiode dark current, should be suppressed and calibrated. FIG. 18 shows real-time measured optical sensor outputs at two different sensor pixels for the bioluminescence experiment with human ovarian cancer cells. As shown in FIG. 18, the photodiode biasing voltage $V_{PD}$ is set as 0.4V to minimize the dark current. Moreover, dark current in each sensing pixel is recorded before the measurement and then subtracted after the bioluminescence recoding.

During the bioluminescence measurement, the culture medium is first removed and immediately replaced with medium supplemented with 200 µg/mL of luciferin at T=0. The CMOS sensor chip starts data recording after a 130-second setup time. During the optical detection, the photodiode reset pulse width is 1 second and the repetition rate is 0.05 Hz. Thus, each photo current integration window is 19 seconds, and the optical detection data is refreshed every 20 seconds. The optical sampling rate is sufficient to record the bioluminescence emission and can be increased if needed. The Correlated Double Sampling (CDS) technique is employed in this example. The measured bioluminescence emission peaks at around 300 seconds (5 minutes) after the luciferin administration and fully decays after 800 seconds (13.3 minutes). This data agrees well with the luciferin mechanistic effect. This real-time bioluminescence experiment demonstrates that the CMOS sensor array chip is capable of measuring low-intensity optical signals and supports bioluminescence as one of the sensing modalities.

Joint Modality Cellular Measurement with 2D Impedance Mapping and Optical Shadow Imaging One of the unique advantages of the described multi-modality cellular sensor array is its capability of real-time joint-modality measurement of the same cellular samples, so that the living cells and tissues can be holistically characterized.

In one example, as described with respect to FIGS. 8B and 8C, the CMOS sensor performs a joint-modality cellular measurement with 2D impedance mapping and optical shadow imaging modes. As previously described, the 2D impedance mapping monitors the cell attachment, while the optical shadow imaging can track the location and area information of the cells. On-chip cultured GFP labeled MN aggregates were used in this joint-modality experiment.

After the MNs are seeded onto the CMOS chip and reach maturation, the fluorescent imaging was first performed using standard fluorescent microscope as the reference imaging (see FIG. 8A). Then, the optical shadow imaging of the MNs were captured using the underlying CMOS multi-modality sensor array chip. Since both images provide the 2D location and area information of the MN aggregates, a close matching can be found between the two images and shows the functionality of the optical shadow imaging. After performing the optical shadow imaging, the 2D cellular impedance mapping was performed by the CMOS sensor array chip with an excitation frequency of 1 MHz. It should be understood that the order of tests shown here is merely illustrative and not indicative of a required order of testing. In addition, although static images are shown in FIGS. 8B and 8C, the multi-modality measurements by the CMOS chip are actually performed in a real-time fashion and may be time-interleaved.

The joint-modality characterization described above provides additional cell information and cannot be achieved by single-modality sensing. These real-time multi-modality measurement results thus demonstrate the unique advantage of the proposed multi-modality sensor.

Joint Modality Cellular Measurement with Voltage Recording and Impedance Sensing The joint-modality cellular measurement of the CMOS sensor array chip was further performed in a cell-based assay to demonstrate its drug screening capability. On-chip cultured human cardiomyocytes was used in this experiment. Their autonomous beating is captured by the extracellular voltage recording, and the beating rate is used to characterize the potency of the cardiac drugs. Isoproterenol, a small molecule cardiac drug, is used in this example. Isoproterenol has its known drug effect of activating the $\beta_1$-receptors on the cardiac cells and increasing the cardiac cells beating rate. It has been widely used to treat bradycardia and heart block.

Figure 19:
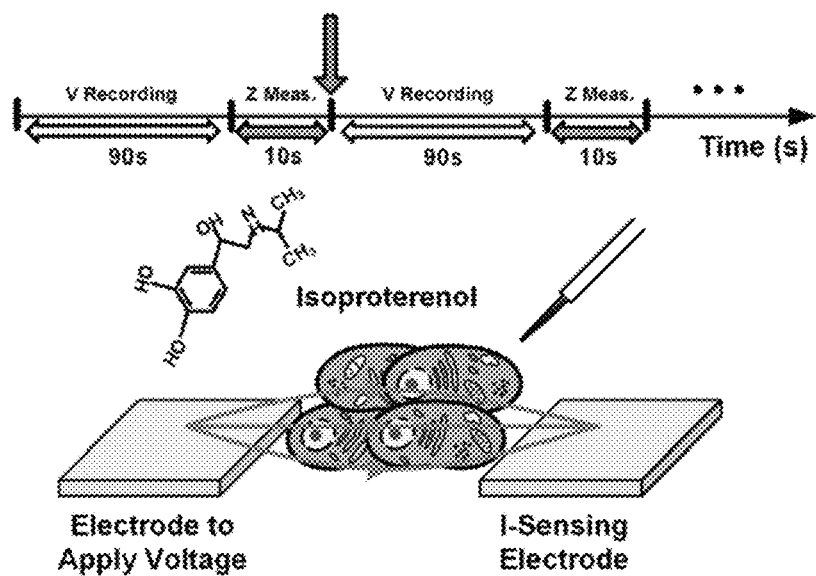
FIG. 19 illustrates the cardiac drug screening experiment and includes the time sequence of the extracellular voltage recording and cellular impedance sensing joint-modality measurements for cardiac drug screening and characterization.
Figure 20:
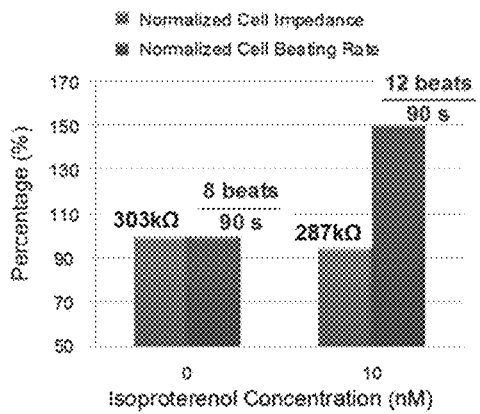
FIG. 20 shows a plot of the results of the cardiac drug screening and characterization example experiment.

First, the on-chip cardiomyocytes beating spikes were recorded as the extracellular voltage recording in a normal culture medium. The baseline cellular impedance mapping was also measured. Next, 10 nM isoproterenol was directed to the cell culture medium using pipettes, and the cardiomyocytes are real-time monitored with joint-modality measurements. Each measurement window is 100 seconds with 90 seconds for the extracellular voltage recording to characterize the cardiomyocytes beating and 10 seconds for the cellular impedance measurement. FIG. 19 illustrates the cardiac drug screening experiment and includes the time sequence of the extracellular voltage recording and cellular impedance sensing joint-modality measurements for cardiac drug screening and characterization. FIG. 20 shows a plot of the results of the cardiac drug screening and characterization example experiment.

After 10 nM isoproterenol administration, the recorded number of cell beating spikes in the 90-second counting window increases by 150%, well matching the isoproterenol mechanism. Referring to FIG. 20, it can be seen that the real-time cardiomyocytes impedance only shows a small decrease, indicating that the cell attachment is not significantly affected by isoproterenol. Therefore, the multi-modality sensor array enables holistic cell characterization with real-time multi-physics measurements, which potentially opens the door for future low-cost high-volume high-content drug screening.

It should be understood that the examples and embodiments described herein are for illustrative purposes only and that various modifications or changes in light thereof will be suggested to persons skilled in the art and are to be included within the spirit and purview of this application.

What is claimed is:

1. A multi-modality sensor array for physiological characterization of cells, the sensor array being implemented in 130 nm or larger CMOS technology nodes and comprising:
   an array of sensing pixel groups, each sensing pixel group comprising an array of sensing pixels, each sensing pixel at least comprising a shared operational amplifier (op amp);
   a plurality of signal conditioning blocks, each signal conditioning block coupled to a corresponding one sensing pixel group of the array of sensing pixel groups to process outputs of that sensing pixel group; and a controller providing signals for independent configuration of sensing modalities for each sensing pixel of each sensing pixel group.

2. The sensor array of claim 1, wherein each sensing pixel supports at least two sensing modalities.

3. The sensor array of claim 2, wherein one of the at least two sensing modalities comprises electrical impedance mapping, the sensor further comprising:
    a quadrature signal generator;
    an impedance testing signal generator receiving a signal from the quadrature signal generator to generate a voltage signal for impedance mapping; and
    a buffer circuit for each sensing pixel group with corresponding mixer distribution transmission lines, the buffer circuit coupled to receive a selected in-phase or quadrature signal from the quadrature signal generator,
    wherein each signal conditioning block comprises a down-converter mixer coupled to the corresponding mixer distribution transmission lines for its corresponding sensing pixel group and the output for its corresponding sensing pixel group,
    wherein each sensing pixel group comprises a MUX for selecting pixels for applying voltage signals to achieve impedance mapping, the MUX receiving the voltage signal for impedance mapping from the impedance testing signal generator.

4. The sensor array of claim 3, wherein each sensing pixel comprises at least:
    the shared op amp, wherein the op amp has an inverting input and a non-inverting input;
    an in-pixel pad coupled to the inverting input of the op amp;
    a first switch, receiving a corresponding first signal from the controller, for connecting the inverting input of the op amp to a node at an output of the op amp;
    a second switch, receiving a corresponding second signal from the controller, for connecting the output of the op amp to the node; and
    a third switch, receiving a corresponding third signal from the controller, connecting the node to a pixel output,
    wherein the voltage signal for impedance mapping is coupled to the node by the MUX.

5. The sensor array of claim 2, wherein one of the at least two sensing modalities comprises electrical voltage recording, the sensor further comprising:

a reference circuit for each sensing pixel group, the reference circuit comprising a pad for connection to a cellular environment.

6. The sensor array of claim 5, wherein each sensing pixel comprises at least:
    the shared op amp, wherein the op amp has an inverting input and a non-inverting input, wherein a signal from the reference circuit is coupled to the non-inverting input; and
    an in-pixel pad coupled to the inverting input of the op amp.

7. The sensor array of claim 2, wherein one of the at least two sensing modalities comprises optical detection, each sensing pixel comprising:
    an optical sensing circuit comprising a photodiode.

8. The sensor array of claim 1, wherein each sensing pixel group further comprises a temperature sensor.

9. The sensor array of claim 1, wherein each sensing pixel group further comprises a pixel selection MUX that, under control of the controller, selectively connects each sensing pixel of its sensing pixel group to the corresponding signal conditioning block for signal processing.

10. The sensor array of claim 1, wherein each signal conditioning block comprises a low pass filter and variable gain amplifier.

11. The sensor array of claim 1, wherein the controller comprises a serial to parallel interface for each sensing pixel group.

12. A method of physiological characterization comprising:
    applying a cellular culture to the multi-modality sensor of claim 1; and
    performing a biological measurement on the cellular culture using at least two sensing modalities of the multi-modality sensor.

13. The method of claim 12, further comprising:
    applying at least one biochemical stimulus to the cellular culture on the multi-modality sensor array before, during, or after using one or more of the at least two sensing modalities.

14. The method of claim 13, wherein the stimulus is a chemical/drug or a pathogen.

15. The method of claim 12, wherein performing the biological measurement on the cellular culture comprises:
    performing voltage recording and impedance mapping.

16. The method of claim 12, wherein performing the biological measurement on the cellular culture comprises:
    performing impedance mapping and optical detection.

* * * * *